United States Patent [19]
Odorisio et al.

[11] Patent Number: 4,751,319
[45] Date of Patent: Jun. 14, 1988

[54] 1,3,2-OXAZAPHOSPHOLDINE STABILIZERS

[75] Inventors: Paul A. Odorisio, Edgewater, N.J.; Stephen D. Pastor, Yonkers, N.Y.; James L. Hyun, Danbury, Conn.

[73] Assignee: Ciba-Geigy Corporation, Ardsley, N.Y.

[21] Appl. No.: 9,430

[22] Filed: Feb. 2, 1987

Related U.S. Application Data

[63] Continuation-in-part of Ser. No. 855,059, Apr. 23, 1986, abandoned.

[51] Int. Cl.$^4$ .............................................. C07F 9/22
[52] U.S. Cl. ........................................ 558/76; 558/81; 524/117; 524/119
[58] Field of Search ................................. 558/81, 76

[56] References Cited
U.S. PATENT DOCUMENTS

2,865,948  12/1958  Fusco ..................................... 558/81
3,172,903   3/1965  Reetz et al. ............................ 558/81

Primary Examiner—Anton H. Sutto
Attorney, Agent, or Firm—Harry Falber

[57] ABSTRACT

1,3,2-oxazapholidine derivatives of the formula

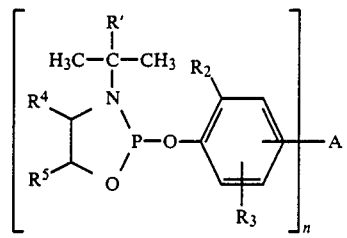

are effective in stabilizing organic materials against oxidative, thermal and actinic degradation, said derivatives being particularly effective as color improvers and process stabilizers in organic materials containing phenolic antioxidants.

15 Claims, No Drawings

1,3,2-OXAZAPHOSPHOLDINE STABILIZERS

Organic polymeric materials such as plastics and resins are subject to thermal, oxidative and photodegradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

Various oxazapholidine compounds have been previously disclosed for a number of different uses. For example, U.S. 2,865,948 discloses aroxy-substituted oxazapholidines wherein the end products exhibit pentavalent phosphorus. In addition, certain corresponding trivalent phosphorus compounds are recited as intermediates. These materials are noted for their insecticidal utility. U.S. Pat. No. 3,172,903 discloses 1,3,2-oxazapholidines having substitution on the ring nitrogen atom and a variety of aminoethoxy substituents linked to the phosphorus atom. These compounds are noted as fungicides. Various 1,3,2-oxazapholidines with substituents on the ring nitrogen atoms and aroxy substituents on the phosphorus atom are disclosed in U.S. Pat. No. 3,795,612 as antioxidants primarily for lubricants and greases. Organo-phosphorus compounds are noted in U.S. Pat. No. 3,990,994 as components of a polymerization catalyst. U.S. Pat. No. 4,071,583 discloses N-substituted and (PO)-substituted oxazapholidines useful as intermediates in the preparation of polymers. Diaza- rather than oxazapholidines are disclosed in DDR No. 146,464 as antioxidants for polyolefins.

It has now been determined that the oxazapholidines of this invention exhibit a variety of desirable properties which makes them particularly effective and useful as stabilizers. Thus, the compounds serve to protect various substrates such as polyolefins, elastomers and lubricating oils against the adverse effects of oxidative and thermal degradation. They are most effective as color improvers and process stabilizers in polyolefin compositions which may contain metal salts of fatty acids and which also contain a phenolic antioxidant. Thus, they serve to substantially reduce color formation resulting from the presence of the phenolic antioxidant and/or from the processing conditions as well as to directly protect the polymer from said processing conditions. They also prevent the discoloration of polyolefin compositions containing hindered amine light stabilizers or combinations of phenolic antioxidants and organic phosphites. In addition, the gas fading that may be experienced upon exposure to the combustion products of natural gas is also significantly reduced.

In summary, the compounds of this invention are unique and exhibit surprising properties distinct from the prior art compounds. The advantages that the instant 1,3,2-oxazapholidines exhibit over the prior art can be grouped as follows:

(1) They exhibit superior polymer stabilizing properties during processing.
(2) They provide for low color development when used in combination with conventional phenolic stabilizers.
(3) They exhibit superior light stabilizing and long term heat aging properties in polymeric substrates.
(4) They exhibit low volatility which has the advantage of low loss from polymeric substrates during thermal processing.
(5) They exhibit resistance to moisture pick-up and hydrolysis.

Accordingly, it is the primary object of this invention to provide a class of 1,3,2-oxazapholidine derivatives which exhibits a broad range of improved stabilization performance characteristics.

It is a further object of this invention to provide compositions of organic materials stabilized against oxidative, thermal and actinic degradation by the presence therein of said derivatives.

It is still a further object to provide such compositions which also contain phenolic antioxidants wherein said derivatives substantially reduce color formation resulting from the presence of said phenols.

Various other objects and advantages of this invention will become evident from the following description thereof.

The compounds of this invention correspond to the formula

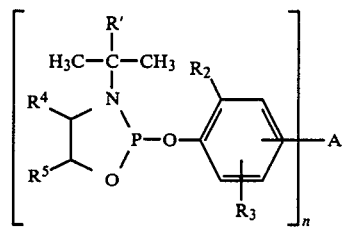

wherein
R' is alkyl of 1 to 5 carbon atoms, cycloalkyl of 5 to 6 carbon atoms, phenyl, phenyl substituted by alkyl of 1 to 18 carbon atoms, aralkyl of 7 to 9 carbon atoms or said aralkyl substituted by alkyl of 1 to 18 carbon atoms;

$R^2$ is alkyl of 1 to 18 carbon atoms, cycloalkyl of 5 to 6 carbon atoms, phenyl, phenyl substituted by alkyl of 1 to 18 carbon atoms, aralkyl of 7 to 9 carbon atoms or said aralkyl substituted by alkyl of 1 to 18 carbon atoms;

$R^3$, $R^4$ and $R^5$ independently are hydrogen or $R^2$;

$R^4$ and $R^5$ together with the ring carbon atoms may also form a cycloalkyl ring of 5 to 6 carbon atoms;

n is 1–5;

A is hydrogen, a direct bond, an n-valent aliphatic hydrocarbon of 1 to 18 carbon atoms, an n-valent aromatic or aromatic aliphatic hydrocarbon of 6 to 20 carbon atoms, a group of the formula

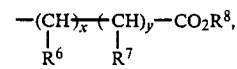

—$SR^9$, —$OR^{10}$ or —$NR^{11}R^{12}$, or —S—,

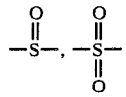

or —O— when n=2, wherein

R[6] and R[7] are independently a substituent defined under R[3],

R[8] is R[3], an n-valent aliphatic hydrocarbon of 1 to 10 carbon atoms or an n-valent aromatic or aromatic aliphatic hydrocarbon of 6 to 10 carbon atoms, R[9], R[10], R[11] and R[12] are independently a substituent defined under R[2], and x and y are independently 0, 1 or 2.

Alkyl in the various R groups is straight-chain or branched alkyl such as methyl, ethyl, n-propyl, isopropyl, n-butyl, tert-butyl, n-pentyl, n-hexyl, 2-ethylhexyl, n-octyl, decyl, dodecyl and octadecyl; cycloalkyl is cyclopentyl or cyclohexyl; and aralkyl is preferably benzyl, α-methylbenzyl and α,α-dimethylbenzyl.

A as a monovalent aliphatic hydrocarbon can be e.g. $C_1$–$C_{20}$ alkyl, including the members defined hereinabove, and in addition, tridecyl, tetradecyl, pentadecyl, hexadecyl and heptadecyl, or $C_5$–$C_6$ cycloalkyl such as cyclopentyl or cyclohexyl.

A as a monovalent aromatic hydrocarbon can be, for example, phenyl which can be substituted by $C_1$–$C_4$ alkyl and hydroxy, such as e.g. tolyl, xylyl, mesityl, 3,5-di-methyl-4-hydroxy-phenyl, 3,5-di-tert-butyl-4-hydroxyphenyl, etc. or $C_7$–$C_{10}$ aralkyl substituted by $C_1$–$C_4$ alkyl and hydroxy such as for example 3,5-di-tert-butyl-4-hydroxybenzyl or particularly 2-(3,5-di-tert-butyl-4-hydroxyphenyl)ethyl.

A as a bivalent hydrocarbon can be e.g. straight-chain or branched $C_2$–$C_{10}$ alkylene or $C_2$–$C_6$-alkylidene such as, for example, ethylene, ethylidene, trimethylene, tetramethylene, pentamethylene, 2,2-dimethylpropane-1,3-diyl, hexamethylene, heptamethylene, octamethylene, decamethylene, 2,2-pentamethylene-propane-1,3-diyl, and cyclohexylene or $C_6$–$C_{10}$ arylene such as phenylene, phenylene substituted by one or more $C_1$–$C_4$ alkyl or naphthylene.

A as a trivalent, tetravalent or pentavalent hydrocarbon can be a group of the following formulae

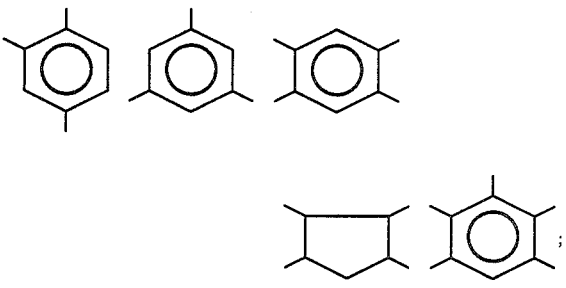

alkanetriyl of 3 to 6 carbon atoms, such as glyceryl or trimethylyl propane; or alkanetetrayl of 4 to 6 carbon atoms such as pentaerythrityl.

Representative substituted propionic acid substituents as A include methyl propionate, octadecyl propionate or methyl-2-methyl propionate. Typical ether, thioether and amino A substituents include phenyl ether, octadecyl ether, phenyl thioether, methyl-3-thiopropionate or N-methylanilino.

Various preferred combinations of substituents and substituent patterns include R' as methyl and R[2] as $C_1$–$C_4$ alkyl; n=1, R[3] and A as alkyl and R[3] and A attached to the 4- and 6-positions, respectively, of the phenyl ring; n=2 and A as $C_2$–$C_3$ alkylidene or a direct bond; and A as 2-(carboalkoxy)ethyl, 2-(carboaroxy)ethyl or a 2-(carboxy)ethyl with R[8] as the n-valent hydrocarbon substituent.

The derivatives of this invention are prepared by reacting the appropriately substituted phenol or hydroxyphenyl propionate

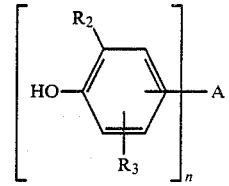

with the appropriately substituted 2-chloro-1,3,2-oxazaphospholidine in an appropriate solvent system to yield the desired product. The solvent system is preferably a heterocyclic ether such as tetrahydrofuran or an aromatic hydrocarbon such as benzene, toluene or xylene. The reaction temperature ranges from −30° to 150° C. The preferred method involves conducting the reaction in the presence of a proton acceptor including metal hydrides such as sodium hydride, lithium hydride, calcium hydride or potassium hydride; alkali and alkaline-earth metal hydroxides such as sodium hydroxide or potassium hydroxide; or metal alkoxides such as sodium methoxide, sodium ethoxide or potassium tert-butoxide.

An alternate approach which allows for the in-situ preparation of the 1,3,2-oxazaphospholidine involves reacting approximately stoichiometric amounts of phosphorus trichloride and the appropriately 2-substituted aminoethanol in a solvent system. The solvent is preferably an ether such as diethylether, tetrahydrofuran or 1,2-dimethoxyethane, or an aromatic hydrocarbon such as benzene, toluene or xylene. The reaction temperature ranges from −30° to 150° C. and the reaction can be conducted in the presence of a proton acceptor such as a tertiary amine, for example, triethylamine or pyridine, but preferably without the use of such a proton acceptor. Thereafter, the appropriately substituted phenol or hydroxyphenyl propionate is added in a comparable solvent and the reaction completed generally at room temperature.

The starting materials needed to prepare the derivatives of this invention are items of commerce or can be prepared by known methods. In this regard, typical hydroxyphenyl-containing reactants include:

2,2'-methylene bis (4,6-di-tert-butylphenol)
2,2'-methylene bis (4-methyl-6-tert-butylphenol)
2,2'-methylene bis (4-ethyl-6-tert-butylphenol)
2,2'-methylene bis [4-methyl-6-(1-methylcyclohexyl)-phenol]
4,4'-isopropylidene bis(2-tert-butylphenol)
2,2'-methylene bis (4-methyl-6-cyclohexylphenol)
2,2'-thio-bis(4-methyl-6-tert-butylphenol)
4,4'-thio-bis(6-tert-butyl-3-methylphenol)
4,4'-thio-bis(2-tert-butyl-6-methylphenol)
4,4'-butylidene bis(6-tert-butyl-meta-cresol) thiodiethylene bis-(3,5-di-tert-butyl-4-hydroxy)hydrocinnamate
N,N'-hexamethylene bis(3,5-di-tert-butyl-4-hydroxyhydrocinnamamide)

2,2-dimethyl-1,3-propanediyl bis(3,5-di-tert-butyl-4-hydroxy)hydrocinnamate tetrakis[methylene(3,5-di-tert-butyl-4-hydroxy-hydrocinnamate)methane 1,3,5-trimethyl-2,4,6-tris(3,5-di-tert-butyl-4-hydroxybenzyl)benzene 1,3,5-tris(3,5-di-tert-butyl-4-hydroxybenzyl)isocyanurate 1,3,5-tris(4-tert-butyl-3-hydroxy-2,6-dimethylbenzyl) 2,6-dimethylbenzyl)-s-triazine-2,4,6-(1H, 3H, 5H)trione 2,2'-oxamido-bisethyl-3-(3,5-di-tert-butyl-4-hydroxyphenyl)propionate triethylene glycol bis[3-(3'-tert-butyl-4'-hydroxy-5'-methylphenyl)propionate]

With regard to the di- and poly-functional phenols, all of the possible stereoisomers which are predictable with respect to having multiple asymmetric centers at the phosphorus, are deemed to be included within the scope of this invention.

The compounds of the present invention are particularly effective in stabilizing organic materials subject to oxidative, thermal and actinic degradation, such as plastics, polymers and resins.

Substrates in which these compounds are particularly useful are polyolefins such as polyethylene and polypropylene; polystyrene, including impact polystyrene, ABS resin, SBR, isoprene, as well as natural rubber, polyesters including polyethylene terephthalate and polybutylene terephthalate, including copolymers, and lubricating oils such as those derived from mineral oil.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under (1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.
18. Polycarbonates.
19. Polysulfones, polyethersulfones and polyetherketones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.
23. Thermosetting acrylic resins, derived from substituted acrylic esters, such as epoxy-acrylates, urethane-acrylates or polyester acrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides.
26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methylcellulose.
27. Mixtures of polymers as mentioned above, for example PP/EPDM, Polyamide 6/EPDM or ABS, PVC/EVA, PVC/ABS, PVC/MBS, PC/ABS, PBTP/ABS.
28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.
29. Aqueous emulsions of natural or synthetic rubber, e.g. natural latex or latices of carboxylated styrene/butadiene copolymers.

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants
  1.1. Alkylated monophenols, for example,
  2,6-di-tert.butyl-4-methylphenol
  2-tert.butyl-4,6-dimethylphenol
  2,6-di-tert.butyl-4-ethylphenol
  2,6-di-tert.butyl-4-n-butylphenol
  2,6-di-tert.butyl-4-i-butylphenol
  2,6-di-cyclopentyl-4-methylphenol
  2-(α-methylcyclohexyl)-4,6-dimethylphenol
  2,6-di-octadecyl-4-methylphenol
  2,4,6-tri-cyclohexylphenol
  2,6-di-tert.butyl-4-methoxymethylphenol
  1.2. Alkylated hydroquinones, for example,
  2,6-di-tert.butyl-4-methoxyphenol
  2,5-di-tert.butyl-hydroquinone
  2,5-di-tert.amyl-hydroquinone
  2,6-diphenyl-4-octadecyloxyphenol
  1.3. Hydroxylated thiodiphenyl ethers, for example
  2,2'-thio-bis-(6-tert.butyl-4-methylphenol)
  2,2'-thio-bis-(4-octylphenol)
  4,4'-thio-bis-(6-tert.butyl-3-methylphenol)
  4,4'-thio-bis-(6-tert.butyl-2-methylphenol)
  1.4. Alkyliden-bisphenols, for example,
  2,2'-methylene-bis-(6-tert.butyl-4-methylphenol)
  2,2'-methylene-bis-(6-tert.butyl-4-ethylphenol)
  2,2'-methylene-bis-[4-methyl-6-(α-methylcyclohexyl)-phenol]
  2,2'-methylene-bis-(4-methyl-6-cyclohexylphenol)
  2,2'-methylene-bis-(6-nonyl-4-methylphenol)
  2,2'-methylene-bis-[6-(α-methylbenzyl)-4-nonylphenol]
  2,2'-methylene-bis-[6-(α,α-dimethylbenzyl)-4-nonylphenol]
  2,2'-methylene-bis-(4,6-di-tert.butylphenol)
  2,2'-ethylidene-bis-(4,6-di-tert.butylphenol)
  2,2'-ethylidene-bis-(6-tert.butyl-4-isobutylphenol)
  4,4'-methylene-bis-(2,6-di-tert.butylphenol)
  4,4'-methylene-bis-(6-tert.butyl-2-methylphenol)
  1,1-bis-(5-tert.butyl-4-hydroxy-2-methylphenyl-butane
  2,6-di-(3-tert.butyl-5-methyl-2-hydroxybenzyl)-4-methylphenol phenol
  1,1,3-tris-(5-tert.butyl-4-hydroxy-2-methylphenyl)-butane
  1,1-bis-(5-tert.butyl-4-hydroxy-2-methylphenyl)-3-n-dodecylmercaptobutane
  ethylenglycol-bis-[3,3-bis-(3'-tert.butyl-4'hydroxyphenyl)-butyrate]
  di-(3-tert.butyl-4-hydroxy-5-methylphenyl)-dicyclopentadiene
  di-[2-(3'-tert.butyl-2'-hydroxy-5'-methyl-benzyl)-6-tert.butyl-4-methylphenyl]-terephthalate.
  1.5. Benzyl compounds, for example,
  1,3,5-tri-(3,5-di-tert.butyl-4-hydroxybenzyl)-2,4,6-trimethylbenzene-di-(3,5-di-tert.butyl-4-hydroxybenzyl)sulfide
  3,5-di-tert.butyl-4-hydroxybenzyl-mercapto-acetic acid isooctyl ester
  bis-(4-tert.butyl-3-hydroxy-2,6-dimethylbenzyl)dithiolterephthalate
  1,3,5-tris-(3,5-di-tert.butyl-4-hydroxybenzyl)-isocyanurate
  1,3,5-tris-(4-tert.butyl-3-hydroxy-2,6-dimethylbenzyl)isocyanurate
  3,5-di-tert.butyl-4-hydroxybenzyl-phosphoric acid-dioctadecyl ester
  3,5-di-tert.butyl-4-hydroxybenzyl-phosphoric acid-monoethyl ester, calcium-salt
  1.6. Acylaminophenols, for example,
  4-hydroxy-lauric acid anilide
  4-hydroxy-stearic acid anilide
  2,4-bis-octylmercapto-6-(3,5-tert.butyl-4-hydroxyanilino-s-triazine
  octyl-N-(3,5-di-tert.butyl-4-hydroxyphenyl)-carbamate 1.7. Esters of β-(3,5-di-tert-butyl-4-hydroxyphenyl)-propionic acid with monohydric or polyhydric alcohols, for example,
methanol; diethyleneglycol;
octadecanol; triethyleneglycol
1,6-hexanediol; pentaerythritol
neopentylglycol; tris-hydroxyethyl isocyanurate
thiodiethyleneglycol; di-hydroxyethyl oxalic acid diamide 1.8. Esters of β-(5-tert-butyl-4-hydroxy-3-methylphenyl)propionic acid with monohydric or polyhydric alcohols, for example,
methanol; diethyleneglycol;
octadecanol; triethyleneglycol
1,6-hexanediol; pentaerythritol
neopentylglycol; tris-hydroxyethyl isocyanurate
thiodiethyleneglycol; di-hydroxyethyl oxalic acid diamide 1.9 Amides of β-(3,5-di-tert.butyl-4-hydroypheyl)propionic acid for example,
N,N'-di-(3,5-di-tert.butyl-4-hydroxypheylpropionyl)-hexamethylenediamine
N,N'-di-(3,5-di-tert.butyl-4-hydroxyphenylpropionyl)-trimethylenediamine
N,N'-di-(3,5-di-tert.butyl-4-hydroxyphenylpropionyl)-hydrazine 2. UV absorbers and light stabilisers 2.1. 2-(2'-Hydroxyphenyl)-benzotriazoles, for example, the 5'-methyl-, 3',5'-di-tert.butyl-, 5'-tert.butyl-, 5'-(1,1,3,3-tetramethylbutyl)-, 5-chloro-3',5'-di-tertbutyl-, 5-chloro-3'-tert.butyl-5'-methyl-, 3'-sec.butyl5'-tert.butyl-, 4'-octoxy, 3',5'-di-tert amyl-, 3',5'-bis-(α,α-dimethylbenzyl)-derivative.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivative.

2.3. Esters of optionally substituted benzoic acids for example, phenyl salicylate, 4-tert.butyl-phenylsalicylate, octylphenyl salicylate, dibenzoylresorcinol, bis-(4-tert.butylbenzoyl)-resorcinol, benzoylresorcinol, 3,5-di-tert.butyl-4-hydroxybenzoic acid 2,4-di-tert.butyl-phenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxycinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert.butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)-sebacate, bis-(1,2,2,6,6-pentamethylpiperidyl)-sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert.octylamino-2,6-dichloro-1,3,5-s-triazine, -tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides, for example, 4,4'-dioctyloxyoxanilide, 2,2'-di-octyloxy-5,5'-di-tert.butyloxanilide, 2,2'-di-dodecyloxy-5,5'-di-tert.butyl-oxanilide, 2-ethoxy-2'-ethyl-oxanilide, N,N'-bis (3-dimethylaminopropyl)oxalamide, 2-ethoxy-5-tert.butyl-2'-ethyloxanilide and its mixture with 2-ethoxy-2'-ethyl-5,4'-di-tert.butyloxanilide and mixtures of ortho- and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythrit diphosphite, tris-(2,4-di-tert.butylphenyl) phosphite, di-isodecylpentaerythritol diphosphite, di-(2,4-di-tert.butylphenyl)pentaerythritol diphosphite, tristearylsorbite triphosphite, tetrakis-(2,4-di-tert.butylphenyl)-4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythritol-tetrakis-(β-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibers, asbestos, talc, kaolin, mica, barium sulfate, metal oxides and hydroxides, carbon black, graphite.

10. Other additives, for example, plasticizers, lubricants, emulsifiers, pigments, optical brighteners, flameproofing agents, anti-static agents, blowing agents and thiosynergists such as dilaurylthiodipropionate or distearyl-thiodipropionate.

While the instant oxazapholidines can be beneficially used as stablizers for a variety of substrates, particularly the polyolefins, both alone and in conjunction with other coadditives, the introduction of the instant oxazapholidines into polyolefins, optionally containing various alkali metal, alkaline earth metal and aluminum salts of higher fatty acids (see Additive #7 hereinabove), with hindered phenolic antioxidants results in enhanced and particularly salubrious protection to such substrates in terms of reducing color formation stemming from the presence of the phenols. Such phenolic antioxidants include n-octadecyl 3,5-di-tert-butyl-4-hydroxyhydrocinnamate, neopentanetetrayl tetrakis-(3,5-di-tert-butyl-4-hydroxyl-hydrocinnamate), di-n-octadecyl 3,5-di-tert- butyl-4-hydroxybenzyl-phosphonate, 1,3,5-tris-(3,5-di-tert-butyl-4-hydroxy-benzyl-)isocyanurate, thiodiethylene bis(3,5-di-tert-butyl-4-hydroxyhydrocinnamate), 1,3,5-trimethyl-2,4,6-tris (3,5-di-tert-butyl-4-hydroxy-benzyl)-benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocyanurate, 1,1,3-tris-(2-methyl-4-hydroxy-5-tert-butylphenyl)butane, 1,3,5-tris-[2-(3,5-di-tert-butyl-4-hydroxyhydrocinnamoyloxy)-ethyl]-isocyanurate, 3,5-di-(3,5-di-tert-butyl-4-hydroxybenzyl)-mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl-3,5-di-tert-butyl-4-hydroxybenzylphosphonate), ethylene bis[3,3-di(3-tertbutyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis-[2-(3,5-tert-butyl-4-hydroxyhydroxocinnamoyloxy)ethyl]-oxamide, and preferably neopentanetetrayl tetrakis( 3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris-(3,5-di-tert-butyl-4-hydroxybenzyl)isocyanurate, 2,6-di-tert-butyl-p-cresol or 2,2'-ethylidene-bis(4,6-di-tert-butylphenol).

Likewise, the instant compounds prevent color formation when hindered amine light stabilizers are present, such hindered amines including bis(1,2,2,6,6-pentamethyl-4-piperidyl)-2-n-butyl-2-(3,5-di-tert-butyl-4-hydroxybenzyl) malonate; bis(2,2,6,6-tetramethyl-4-piperidyl) sebacate; dimethylsuccinate polymer with 4-hydroxy-2,2,6,6-tetramethyl-1-piperidinethanol; and polymer of 2,4-dichloro-6-octylamino-s-triazine with N'-(2,2,6,6-tetramethyl-4-piperidyl)hexamethylene diamine.

The following examples illustrate the embodiments of this invention. In these examples, all parts given are by weight unless otherwise specified.

EXAMPLE 1

3-tert-Butyl-2-(2,6-di-tert-butyl-4-methylphenoxy)-1,3,2-oxazaphospholidine

A 500 ml, three neck flask equipped with a thermometer, an addition funnel and a condenser topped with a nitrogen sweep is charged with 4.4 g (0.11 mol) of sodium hydride. The sodium hydride is washed with two 20 ml portions of hexane and finally suspended in 45 ml of tetrahydrofuran (THF). To the resultant suspension is added dropwise a solution of 22.04 g (0.10 mol) of 2,6-di-tert-butyl-4-methylphenol in 150 ml of THF at such a rate to keep the reaction temperature between 20°–30° C. The resulting yellow solution is warmed to approximately 40° C. for 1 hour and then cooled in an ice bath. A solution of 18.16 g (0.10 mol) of 3-tert-butyl-2-chloro-1,3,2-oxazaphospholidine in 150 ml of THF is added and stirring continued for 16 hours at room temperature. The resulting cloudy mixture is filtered and the solvent evaporated under reduced pressure. The residue is treated with 200 ml of toluene and the resultant suspension filtered. The filtrate is concentrated in vacuo to yield a thick syrup. Triturating with methanol gives 24.5 g (67.0%) of colorless solid: mp 105°–107° C.

Anal. Calcd. for $C_{21}H_{36}NO_2P$: C, 69.01; H, 9.93; N, 3.83. Found: C, 69.3; H, 10.0; N, 3.9.

EXAMPLE 2

3-tert-Butyl-2-(2,4,6-tri-tert-butylphenoxy)-1,3,2-oxazaphospholidine

The procedure of Example 1 is repeated using 2.3 g (0.055 mol) of sodium hydride with 23 ml of THF, 13.12 g (0.05 mol) of 2,4,6-tri-tert-butylphenol in 130 ml of THF, and 9.0 g (0.05 mol) of 3-tert-butyl-2-chloro-1,3,2,oxazaphospholidine in 130 ml of THF to give 9.0 g (44%) of colorless solid: m.p. 73°–74° C.

Anal. Calcd. for $C_{24}H_{42}NO_2P$: C, 70.73; H, 10.39; N, 3.44. Found: C, 70.7; H, 10.5; N, 3.5.

EXAMPLE 3

Hexamethylene bis[3-(3,5-di-tert-butyl-4-(3-tert-butyl-1,3,2-oxazaphospholidin-2-yl-2-oxy)phenyl)propionate]

The procedure of Example 1 is repeated using 3.33 g (0.085 mol) of sodium hydride with 36 ml of THF, 24.54 g (0.038 mol) of hexamethylene bis[3-(3,5-di-tert-butyl-4-hydroxyphenyl)propionate] in 100 ml of THF and 14.78 g (0.081 mol) of 3-tert-butyl-2-chloro-1,3,2,-oxazaphospholidine in 100 ml of THF to give 24.25 g (68.0%) of colorless solid: mp 130°–132° C.

Anal. Calcd. for $C_{52}H_{86}N_2O_8P_2$ C, 67.21; H, 9.33; N, 3.02. Found: C, 67.3; H, 9.2; N, 3.0.

EXAMPLE 4

3-tert-Butyl-2-(2,4,6-trimethylphenoxy)-1,3,2-oxazaphospholidine

The procedure of Example 1 is repeated using 4.4 g (0.11 mol) of sodium hydride with 45 ml of THF, 13.62 g (0.10 mol) of 2,4,6-trimethylphenol in 150 ml of THF and 18.16 g (0.10 mol) of 3-tert-butyl-2-chloro-1,3,2-oxazaphospholidine in 150 ml of THF to give a (75.6%) of colorless liquid: bp. 99°–103° C. (0.01 mm Hg).

Anal. calcd. for $C_{15}H_{24}NO_2P$: C, 64.04; H, 8.6; N, 4.98. Found: C, 64.4; H, 8.4; N, 4.6.

EXAMPLE 5

Bis[2-(3-tert-butyl-1,3,2-oxazaphospholidin-2-yl-2-oxy)-3,5-di-tert-butylbenzene]

The procedure of Example 1 is repeated using 4.4 g (0.11 mol) of sodium hydride with 45 ml of THF, 20.53 g (0.05 mol) of 2,2'-dihydroxy-3,3',5,5'-tetra-tert-butyl-biphenyl in 125 ml of THF and 19.98 g (0.11 mol) of 3-tert-butyl-2-chloro-1,3,2-oxazaphospholidine in 125 ml of THF to give 12.2 g (34.8%) of colorless solid: m.p. 169°–172° C.

Anal. Calcd. for $C_{40}H_{66}N_2O_4P_2$: C, 68.54; H, 9.49; N, 4.00. Found: C, 69.1; H, 9.3; N, 3.9.

EXAMPLE 6

Ethylidene bis[2-(3-tert-butyl-1,3,2-oxazaphospholidin-2-yl-2-oxy)-3,5-di-tert-butylbenzene]

The procedure of Example 1 is repeated using 4.4 g (0.11 mol) of sodium hydride with 45 ml of THF, 21.94 g (0.05 mol) of 2,2'-ethylidine bis(4,6-di-tert-butylphenol) in 125 ml of THF and 18.16 g (0.10 mol) of 3-tert-butyl-2-chloro-1,3,2-oxazaphospholidine in 125

EXAMPLE 7

3-tert-Butyl-2-(2,4-di-tert-butylphenoxy)-1,3,2-oxaza-phospholidine

A solution of 8.7 ml (0.10 mol) of phosphorus trichloride in 200 ml of diethyl ether is cooled at 0° C., in a 1 liter, three neck flask equipped with a mechanical overhead stirrer, a thermometer and an addition funnel, under a nitrogen sweep. A solution of 27.7 ml (0.20 mol) of triethylamine and 11.72 g (0.10 mol) of 2-tert-butylaminoethanol in 50 ml of diethyl ether is added thereto at such a rate that the reaction temperature is kept below 5° C. After the completion of the addition, the reaction mixture is allowed to warm to room temperature and is stirred for 1 hour. To this white cloudy mixture is added a solution of 20.63 g (0.10 mol) of 2,4-di-t-butylphenol and 15.2 ml (0.11 mol) of triethylamine in 50 ml of diethyl ether. This mixture is then stirred for 16 hours at room temperature.

The white insoluble solids are filtered and the filtrate is concentrated under reduced pressure to give a yellow liquid. This liquid is treated with 200 ml of toluene and the resultant suspension is filtered. The filtrate is concentrated under reduced pressure to give 22.25 g (63.3%) of a colorless liquid: b.p. 118°–123° C. (0.01 mm Hg).

Anal. Calcd. for $C_{20}H_{34}NO_2P$: C, 68.35; H, 9.75; N, 3.99. Found: C, 68.0; H, 9.7; N, 4.1

EXAMPLE 8

3-tert-Butyl-2-[2,6-di-tert-butyl-4-(methylpropion-3-yl)phenoxy]-1,3,2-oxazaphospholidine The procedure of Example 1 is repeated using 2.51 g (0.063 mol) of sodium hydride in 27 ml of THF, 16.7 g (0.057 mol) of methyl-3-(3,5-di-tert-butyl-4-hydroxyphenyl)propionate in 100 ml of THF and 10.37 g (0.057 mol) of 3-tert-butyl-2-chloro-1,3,2-oxazaphospholidine in 100 ml of THF to give 24 g (96%) of a colorless glass.

EXAMPLE 9

Bis[4-(3-tert-butyl-1,3,2-oxazaphospholidin-2-yl-2-oxy)-3,5-di-tert-butylphenyl]methane The procedure of Example 1 is repeated using 1.76 g (0.044 mol) of sodium hydride in 18 ml of THF, 8.49 g (0.020 mol) of 4,4'-methylene bis(2,6-di-tert-butylphenol) in 50 ml of THF, and 7.26 g (0.040 mol) of 3-tert-butyl- 2-chloro-1,3,2-oxazaphospholidine in 50 ml of THF to give 5.0 g (35%) of white powder: m.p. 156°–159° C.

Anal. Calcd. for $C_{41}H_{68}N_2O_4P_2$: C, 68.9; H, 9.6; N, 3.9. Found: C, 68.7; H, 9.4; N, 3.9.

EXAMPLE 10

Bis[2-(3-tert-butyl-1,3,2-oxazaphospholidin-2-yl-2-oxy)-3,5-di-tert-butylphenyl]methane The procedure of Example 1 is repeated using 2.2 g (0.055 mol) of sodium hydride in 25 ml of THF, 10.62 g (0.025 mol) of bis(3,5-di-tert-butyl-2-hydroxyphenyl)methane in 60 ml of THF, and 9.08 g (0.050 mole) of 3-tert-butyl-2-chloro-1,3,2-oxazaphospholidine in 60 ml of THF to -chtoro-1,3,2-oxazaphospholidine in 60 ml of THF to give a crystalline foam.

Anal. Calcd. for $C_{41}H_{68}N_2O_4P_2$: C, 68.9; H, 9.6; N, 3.9. Found: C, 68.8; H, 9.8; N, 3.7.

EXAMPLE 11

3-tert-Butyl-2-chloro-1,3,2-oxazaphospholidine (intermediate for Ex. 10)

To a solution of 8.7 ml (0.10 mol) of phosphorus trichloride in 200 ml of toluene in a 500 ml three neck flask equipped with a mechanical stirrer, a condenser and an addition funnel is added a solution of 11.72 g (0.10 mol) of 2-tert-butylaminoethanol in 50 ml of toluene. After refluxing for 16 hours, the orange solids are filtered off and the filtrate concentrated in vacuo. Distillation under reduced pressure gives 10.3 g (56.7%) of clear liquid: b.p. 82° C./1.0 mm Hg.

EXAMPLE 12

Thiodiethylene bis(3-(3,5-di-tert-butyl-4-(3-tert-butyl-1,3,2-oxazaphospholidin-2-yl-2-oxy) phenyl)propionate)

The procedure of Example 1 is repeated using 0.48 g (0.01 mol) of sodium hydride with 5 ml of THF, 3.21 g (0.005 mol) of thiodiethylene bis(3-(3,5-di-tert-butyl-4-hydroxyphenyl)propionate) in 15 ml of THF and 1.82 g (0.01 mol) of 3-tert-butyl-2-chloro-1,3,2-oxazaphospholidine in 15 ml of THF to give 1.8 g (38.6%) of off-white gum.

Anal. Calcd. for $C_{50}H_{82}N_2O_8P_2S$: C, 64.35; H, 8.86; N, 3.00. Found: C, 64.3; H, 9.0; N, 3.0.

EXAMPLE 13

Octadecyl 3-(4-(3-tert-butyl-1,3,2-oxazaphospholidin-2-yl-2-oxy)-3,5-di-tert-butylphenyl) propionate The procedure of Example 1 is repeated using 0.48 g (0.01 mol) of sodium hydride with 5 ml of THF, 5.31 g (0.01 mol) of octadecyl-3-(3,5-di-tert-butyl-4-hydroxyphenyl)propionate in 25 ml of THF and 1.82 g (0.01 mol) of 3-tert-butyl-2-chloro-1,3,2-oxazaphospholidine in 15 ml of THF to give 5.8 g (86%) of colorless syrup.

Anal. Calcd. for $C_{41}H_{74}NO_4P$: C, 72.84; H, 11.03; N, 2.07. Found: C, 72.7; H, 11.3; N, 2.2.

EXAMPLE 14

2,2-Dimethylpropylene bis(3-(3,5-di-tert-butyl-4-(3-tert-butyl-1,3,2-oxazaphospholidin-2-yl-2-oxy)phenyl)propionate The procedure of Example 1 is repeated using 0.88 g (0.022 mol) of sodium hydride with 10 ml of toluene and 0.2 ml (0.001 mol) of tetraglyme, 6.25 g (0.01 mol) of 2,2-dimethylpropylene bis(3-(3,5-di-tert-butyl-4-hydroxyphenyl)propionate) in 25 ml of toluene and 3.63 g (0.02 mol) of 3-tert-butyl-2-chloro-1,3,2-oxazaphospholidine to give 5.4 g (59%) of colorless syrup.

EXAMPLE 15

Bis(2-(3-tert-butyl-1,3,2-oxazaphospholidin-2-yl-2-oxy)-3,5-di-tert-butylphenyl)sulfide The procedure of Example 1 is repeated using 0.88 g (0.022 mol) of sodium hydride with 10 ml of THF, 4.43 g (0.01 mole) of bis(3,5-di-tert-butyl-2-hydroxyphenyl)sulfide in 25 ml of THF and 3.63 g (0.02 mol) of 3-tert-butyl-2-chloro-1,3,2-oxazaphospholidine in 25 ml of THF to give 6.5 g (88%) of foamy solid.

EXAMPLE 16

2,2'-Bis(3-tert-butyl-1,3,2-oxazaphospholidin-2-yl-2-oxy)biphenyl

The procedure of Example 1 is repeated using 0.88 g (0.022 mol) of sodium hydride with 10 ml of THF, 1.86 g (0.01 mol) of 2,2'-dihydroxybiphenyl in 25 ml of THF and 3.63 g (0.02 mol) of 3-tert-butyl-2-chloro-1,3,2-oxazaphospholidine in 25 ml of THF to give 4.0 g (84%) of clear oil.

EXAMPLE 17

1,3-Bis(4-(3-tert-butyl-1,3,2-oxazaphospholidin-2-yl-2-oxy)-3,5-di-tert-butylbenzyl)-5-(3,5-di-tert-butyl-4-hydroxybenzyl)isocyanurate The procedure of Example 1 is repeated using 0.39 g (0.009 mol) of sodium hydride with 5 ml of THF and 0.4 ml of tetraglyme, 2.35 g (0.003 mol) of 1,3,5-tris(3,5-di-tert-butyl-4-hydroxybenzyl)isocyanurate in 15 ml of THF and 1.63 g (0.009 mol) of 3-tert-butyl-2-chloro-1,3,2oxazaphospholidine in 5 ml of THF to give 1.3 g (35.5%) of off-white solid: m.p. 89°-103° C.;

Anal. Calcd. for $C_{66}H_{93}N_5O_8P_2$: C, 67.07; H, 8.73; N, 6.52. Found: C, 67.2; H, 9.1; N, 6.2.

EXAMPLE 18

3-tert-Butyl-2-chloro-5-tetradecyl-1,3,2-oxazaphospholidine (intermediate for Examples 19 and 20)

To a $CO_2(s)$/acetone cooled solution of 10.5 ml (0.077 mol) of phosphorus trichloride in 150 ml of dichloromethane is added dropwise a solution of 24.0 g (0.077 mol) of 1-tert-butylamino-2-hexadecanol and 21.3 ml (0.153 mol) of triethylamine in 37.5 ml of dichloromethane over a five minute period. When the addition is completed, the cooling bath is replaced with a 50° C. water bath for 1 hour. This is then stirred at room temperature for 16 hours.

The insoluble white solids are filtered and the filtrate is concentrated under reduced pressure to give a yellow residue. This is taken up in 100 ml of toluene and the insoluble solids are filtered. The filtrate is concentrated and subsequently distilled under reduced pressure to give 19.2 g (66.4%) of clear liquid. The liquid solidifies upon standing at room temperature: b.p. 190° C. (0.07 mm Hg).

EXAMPLE 19

Hexamethylene bis(3-(3,5-di-tert-butyl-4-(3-tert-butyl-5-tetradecyl-1,3,2-oxazaphospholidin-2-yl-2-oxy)phenyl)propionate)

The procedure of Example 1 is repeated using 0.58 g (0.012 mol) of sodium hydride with 8 ml of THF, 3.83 g (0.006 mol) of hexamethylene bis(3-(3,5-di-tert-butyl 4-hydroxy-phenyl)propionate) in 20 ml of THF and 4.54 g (0.012 mol) of 3-tert-butyl-2-chloro-5-tetradecyl 1,3,2-oxazaphospholidine in 20 ml of THF to give 4.5 g (56.7%) of yellow syrup.

Anal. Calcd. for $C_{80}H_{142}N_2O_8P_2$: C, 72.7; H, 10.8; N, 2.1. Found: C, 72.5; H, 11.1; N, 2.0.

EXAMPLE 20

2,2'-Bis (O-(3-tert-butyl-5-tetradecyl-1,3,2-oxazaphospholidin-2-yl)-4,6-di-tert-butylphenol)

The procedure of Example 1 is repeated using 0.77 g (0.016 mol) of sodium hydride with 10 ml of THF, 3.29 g (0.008 mol) of 2,2'-dihydroxy-3,3',-5,5'-tetra-tert-butylbiphenyl in 25 ml of THF and 6.05 g (0.016 mol) of 3-tert-butyl-2-chloro-5-tetradecyl-1,3,2-oxazaphospholidine in 25 ml of THF to give 4.6 g (52.6%) of yellow syrup.

Anal. Calcd. for $C_{68}H_{122}N_2O_4P_2$: C, 74.68; H, 11.24; N, 2.56. Found: C, 74.4; H, 11.3; N, 2.8.

3-tert-Butyl-2-chloro-4,5-tetramethylene-1,3,2-oxazaphospholidine (intermediate for Example 22)

The procedure of Example 18 is repeated using 32.1 ml (0.234 mol) of phosphorus trichloride in 450 ml of dichloromethane and 40.0 g (0.234 mol) of 3-tert-butylaminocyclohexanol and 65.0 ml (0.468 mol) of triethylamine in 110 ml of dichloromethane to give 42.4 g (81.7%) of clear liquid: b.p. 80°-85° C. (0.1 mm Hg).

EXAMPLE 22

3-tert-Butyl-4,5-tetramethylene-2-(2,4,6-tri-tert-butylphenoxy)-1,3,2-oxazaphospholidine The procedure of Example 1 is repeated using 1.16 g (0.024 mol) of sodium hydride with 15 ml of THF, 6.3 g (0.024 mol) of 2,4,6-tri-tert-butylphenol in 40 ml of THF and 5.32 g (0.024 mol) of 3-tert-butyl-2-chloro-4,5-tetramethylene-1,3,2-oxazaphospholidine in 40 ml of THF to give 5.86 g (52.9%) of white solid: m.p. 115°-117° C.

Anal. Calcd. for $C_{28}H_{48}NO_2P$: C, 72.9; H, 10.5; N, 3.0. Found: C, 72.7; H, 10.5; N, 3.0.

EXAMPLE 23

This example illustrates the thermal stabilizing effectiveness of the instant stabilizers in combination with a phenolic antioxidant in polypropylene.

| Base | Formulation |
|---|---|
| Polypropylene* | 100 parts |
| Calcium Stearate | 0.10 parts |

*Profax 6501 from Hercules Chemical

Stablizers are solvent blended into polypropylene as solutions in methylene chloride and after removal of the solvent by evaporation at reduced pressure, the resin is extruded using the following extruder conditions:

| | Temperature (°C.) |
|---|---|
| Cylinder #1 | 232 |
| Cylinder #2 | 246 |
| Cylinder #3 | 260 |
| Die #1 | 260 |
| Die #2 | 260 |
| Die #3 | 260 |
| RPM | 100 |

The melt flow rate (MFR) is determined by ASTM method 1238 condition L. The melt flow rate is a measure of the molecular weight for a specific type of polymer. The results are shown in Table I.

TABLE I

| | | MFR (g/10 min.) After Extrusion | |
|---|---|---|---|
| | Conc. % | 1 | 5 |
| Additive | | | |
| None | — | 7.8 | 18.0 |
| AO 1[(1)] | 0.1 | 3.8 | 6.6 |
| 0.1% AO 1[(1)] + Additive | | | |
| PS 1[(2)] | 0.05 | 3.0 | 4.1 |

TABLE I-continued

|  | Conc. % | MFR (g/10 min.) After Extrusion | |
|---|---|---|---|
|  |  | 1 | 5 |
| Example 1 | 0.05 | 2.7 | 3.2 |
| Example 2 | 0.05 | 2.7 | 3.3 |
| Example 3 | 0.05 | 3.1 | 3.7 |
| Example 4 | 0.05 | 3.0 | 3.6 |
| Example 5 | 0.05 | 2.7 | 3.1 |
| Example 6 | 0.05 | 3.0 | 3.8 |
| Example 7 | 0.05 | 2.7 | 3.6 |

[1]AO 1 is neopentane tetrayl-tetrakis[3-(3',5'-di-tert-butyl-4'-hydroxyphenyl)propionate]
[2]PS 1 is tris(2,4-di-tert-butylphenyl)phosphite

EXAMPLE 24

This example illustrates the color stabilizing effectiveness of the instant stabilizers in combination with a phenolic antioxidant in polypropylene. After each of the first, third and fifth extrusions, resin pellets from the extruder of Example 23 are compression molded into 125 mil (3.2 mm) thick plaques at 193° C. Specimen yellowness index (Y.I.) is determined according to ASTM D1925. The result are shown in Table II.

TABLE II

|  | Conc. % | YI Color After Extrusion | | |
|---|---|---|---|---|
|  |  | 1 | 3 | 5 |
| Additive |  |  |  |  |
| None | — | 2.5 | 3.7 | 4.8 |
| AO 1[1] | 0.1 | 3.2 | 9.0 | 12.0 |
| 0.1% AO 1[1] + Additive |  |  |  |  |
| PS 1[2] | 0.05 | 2.5 | 6.3 | 11.1 |
| Example 1 | 0.05 | 1.6 | 3.6 | 5.0 |
| Example 2 | 0.05 | 3.3 | 5.7 | 7.0 |
| Example 3 | 0.05 | 2.4 | 5.4 | 7.0 |
| Example 4 | 0.05 | 2.4 | 5.0 | 6.0 |
| Example 5 | 0.05 | 2.0 | 4.6 | 5.6 |
| Example 6 | 0.05 | 3.1 | 5.1 | 6.3 |
| Example 7 | 0.05 | 2.1 | 4.0 | 6.1 |

[1] and [2]-see Example 18

EXAMPLE 25

Resistance to Moisture Pickup

Samples of the stabilizers are exposed to 80% relative humidity at 24° C. The moisture pickup is determined by monitoring the stabilizers' change in weight after 1, 7, 28 and 52 days of exposure. The days of exposure until the maximum weight gain are given in table III.

TABLE III

| Stabilizer | Days of Exposure | Percent Weight Gain |
|---|---|---|
| Example 4 | 7 | 5 |
| Example 7 | 28 | 8 |
| Example 6 | 28 | 0 |
| Example 1 | 52 | 0 |
| Example 2 | 52 | 0 |
| Example 3 | 52 | 0 |
| Example 5 | 52 | 0 |

EXAMPLE 26

Light Stabilization of Polypropylene

This example illustrates the light stabilizing effectiveness of instant stabilizers.

Unstabilized polypropylene powder (Hercules Profax 6501) is thoroughly blended with the indicated amount of additive. The blended materials are then milled on a two-roll mill at 182° C. for five minutes, after which time the stabilized polypropylene is sheeted from the mill and allowed to cool. The milled polypropylene is then cut into pieces and compression molded on a hydraulic press at 220° C. and 175 psi ($1.2 \times 10^6$ Pa) into 5 mil (0.127 mm) films. The sample is exposed in a fluorescent sunlight/black light chamber until failure. Failure is taken as the hours required to reach 0.5 carbonyl absorbance by infrared spectroscopy on the exposed films.

| Additive Compound of | Additive Concentration (% by weight) | FS/BL Test Results (Hours to Failure) |
|---|---|---|
| Base Resin | — | 250 |
| Example 3 | 0.2 | 410 |

EXAMPLE 27

The oxidation stability of milled polypropylene samples, containing the indicated stabilizers, is measured on plaques of 25 mil (0.635 mm) thickness on exposure to air in a forced draft oven at 150° C. The plaques are considered to have failed on showing the first signs of decomposition (e.g., cracking or brown edges).

| Additive Compound of | Additive Concentration | Oxidative Stability Time to Failure (Hours) |
|---|---|---|
| Base Resin | — | <20 |
| Base Resin with 0.3% DSTDP | — | <20 |
| Example 3 | 0.2% | 800 |
| Example 3 with 0.3% DSTDP | 0.1% | 1400 |
| Example 5 | 0.2% | 30 |
| Example 5 with 0.3% DSTDP | 0.1% | 80 |

DSTDP — distearylthiodipropionate

EXAMPLE 28

This example illustrates the long term antioxidant and process stabilizing effectiveness of the instant stabilizers in a rubber.

Antioxidants are evaluated in a medium cis-polybutadiene cement (Firestone Diene 55). After incorporation of stabilizers as cyclohexane solutions, the rubber is isolated by steam coagulation, the crumb washed with water and dried under vacuum at 40° C. Samples for oven aging (70° C., circulating air oven) are prepared by pressing plaques (130 mils) at 100° C. for 3 minutes. Mooney viscosities of the aged and unaged specimens are determined according to ASTM D1646 Part 37. High temperature aging is carried out in a Brabender Plasticorder at 160° C. (60 RPM). The induction time to cross-linking (minutes to an increase in torque) is determined.

| Stabilizer | Mooney Viscosity: ML1 + 4 (100° C.) | | 160° C. Brabender Induction Time (Min) |
|---|---|---|---|
|  | Initial | 4 wk/70° C. |  |
| None | 56 | 74 | 2.0 |
| Example 2 | 52 | 60 | 6.5 |

EXAMPLE 29

This example illustrates the stabilizing effectiveness of the instant stabilizers in polypropylene fiber.

The base formulation comprises 100 parts of unstabilized polypropylene (Profax 6501, Hercules) with 0.10 parts of calcium stearate. Various test stabilizers are solvent blended onto the polypropylene and extruded (one extrusion) as described in Example 23 and pelletized.

The stabilized resin pellets obtained are spun into fibers at 260° C. and the melt flow rate (MFR) is determined by ASTM method 1238 condition L. The melt flow rate is a measure of the molecular weight for a specific type of polymer.

| Stabilizer | Conc. Stabilizer (% by wt.) | MFR (g/10 min.) |
|---|---|---|
| Base formulation | — | 34.7 |
| plus | | |
| Antioxidant A plus | 0.10 | |
| Light stabilizer B plus compound | 0.25 | |
| of Example 5 | 0.10 | 28.7 |
| of Example 6 | 0.10 | 19.5 |

Antioxidant A=neopentanetetrayl tetrakis(3,5-di-tert-butyl-4-hydroxyhydrocinnamate Light stabilizer B=polycondensation product of 2,4-dichloro-6-tert-octylamino-s-triazine and 4,4'-hexamethylenebis(amino-2,2,6,6-tetramethylpiperidine)

The data in Examples 23–29 thus indicate the effective stabilization, color improving and process stabilization performance characteristics of the instant compounds.

Summarizing, it is seen that this invention provides novel compounds which exhibit effective stabilization activity. Variations may be made in proportions, procedures and materials without departing from the scope of the invention as defined by the following claims.

What is claimed is:

1. A compound of the formula $$\left[ \begin{array}{c} \text{structure with } R', H_3C-C-CH_3, R_2, R_4, N, R_5, P-O-\text{phenyl}-A, O, R_3 \end{array} \right]_n$$

wherein

R' is alkyl of 1 to 5 carbon atoms, cycloalkyl of 5 to 6 carbon atoms, phenyl, phenyl substituted by alkyl of 1 to 18 carbon atoms, aralkyl of 7 to 9 carbon atoms or said aralkyl substituted by alkyl of 1 to 18 carbon atoms;

$R^2$ is alkyl of 1 to 18 carbon atoms, cycloalkyl of 5 to 6 carbon atoms, phenyl, phenyl substituted by alkyl of 1 to 18 carbon atoms, aralkyl of 7 to 9 carbon atoms or said aralkyl substituted by alkyl of 1 to 18 carbon atoms;

$R^3$, $R^4$ and $R^5$ independently are hydrogen or $R^2$;

$R^4$ and $R^5$ together with the ring carbon atoms may also form a cycloalkyl ring of 5 to 6 carbon atoms, n is 1–5;

A is hydrogen, a direct bond, an n-valent aliphatic hydrocarbon of 1 to 18 carbon atoms, an n-valent aromatic or aromatic aliphatic hydrocarbon of 6 to 20 carbon atoms, a group of the formula $$-(CH)_x-(CH)_y-CO_2R^8,$$
$$\phantom{-(CH)_x}R^6 \phantom{-(CH)_y}R^7$$

$-SR^9$, $-OR^{10}$ or $-NR^{11}R^{12}$, or $-S-$, $$-\overset{O}{\underset{}{\overset{\|}{S}}}-,\ -\overset{O}{\underset{\underset{O}{\|}}{\overset{\|}{S}}}-$$

or $-O-$ when n=2, wherein $R^6$ and $R^7$ are independently a substituent defined under $R^3$, $R^8$ is $R^3$, an n-valent aliphatic hydrocarbon of 1 to 10 carbon atoms or an n-valent aromatic or aromatic aliphatic hydrocarbon of 6 to 10 carbon atoms, $R^9$, $R^{10}$, $R^{11}$ and $R^{12}$ are independently a substituent defined under $R^2$, and x and y are independently 0, 1 or 2.

2. The compound of claim 1, wherein n=1.

3. The compound of claim 2, wherein A is $C_1$-$C_{20}$ alkyl, $C_5$-$C_6$ cycloalkyl, phenyl, phenyl substituted by $C_1$-$C_4$ alkyl and/or hydroxy, $C_7$-$C_{10}$ aralkyl or $C_7$-$C_{10}$ aralkyl substituted by $C_1$-$C_4$ alkyl and/or hydroxy.

4. The compound of claim 1, wherein n=2.

5. The compound of claim 4, wherein A is a direct bond, $C_2$-$C_{10}$ alkylene, $C_2$-$C_6$ alkylidene, cyclohexylene, $C_6$-$C_{10}$ arylene, $C_6$-$C_{10}$ arylene substituted by $C_1$-$C_4$ alkyl or polymethylene- propane-1,3-diyl.

6. The compound of claim 1, wherein R' is methyl and $R^2$ is $C_1$-$C_4$ alkyl.

7. The compound of claim 3, wherein $R^3$ and A are alkyl and $R^3$ and A are attached to the 6- and 4-positions, respectively, of the phenyl ring.

8. The compound of claim 5, wherein A is $C_2$-$C_3$ alkylidene or a direct bond.

9. 3-tert-Butyl-2-(2,6-di-tert-butyl-4-methyl-phenoxy)-1,3,2-oxazaphospholidine according to claim 2.

10. 3-tert-Butyl-2-(2,4,6-tri-tert-butylphenoxy)-1,3,2-oxazaphospholidine according to claim 2.

11. Hexamethylene bis[3-(3,5-di-tert-butyl-4-3-tert-butyl-1,3,2-oxazaphospholidin-2-yl-2-oxy)phenyl)propionate] according to claim 4.

12. 3-tert-Butyl-2-(2,4,6-trimethylphenoxy)-1,3,2-oxazaphospholidine according to claim 2.

13. Bis[2-(3-tert-butyl-1,3,2-oxazaphospholidin-2-yl-2-oxy)-3,5-di-tert-butylbenzene] according to claim 4.

14. Ethylidene bis[2-(3-tert-butyl-1,3,2-oxazaphospholidin-2-yl-2-oxy)-3,5-di-tert-butylbenzene ] according to claim 4.

15. 3-tert-Butyl-2-(2,4-di-tert-butylphenoxy)-1,3,2-oxazaphospholidine according to claim 2.

* * * * *